United States Patent [19]
Lucas

[11] Patent Number: 5,843,011
[45] Date of Patent: Dec. 1, 1998

[54] SELF ADHESIVE BANDAGE ROLL

[76] Inventor: Gregory Lucas, Box 6651, Santa Rosa, Calif. 95406

[21] Appl. No.: 909,477

[22] Filed: Aug. 11, 1997

[51] Int. Cl.$^6$ ..................................................... A61F 13/00
[52] U.S. Cl. .............................. 602/57; 602/54; 602/56; 206/441
[58] Field of Search .................... 206/440, 441, 206/389; 602/41–59, 900; 221/199, 241, 303

[56] References Cited

U.S. PATENT DOCUMENTS

| | | | |
|---|---|---|---|
| 1,643,926 | 9/1927 | Dickson | 206/441 |
| 2,005,676 | 6/1935 | Hanover | 206/441 |
| 2,133,609 | 10/1938 | Eustis | 206/441 |
| 2,353,332 | 7/1944 | Hall | 206/441 |
| 2,469,064 | 5/1949 | Campbell | 206/441 |
| 2,473,062 | 6/1949 | Kennedey et al. | 206/441 |
| 3,085,024 | 4/1963 | Blackford | 206/441 |
| 4,393,150 | 7/1983 | Kresner | 523/111 |
| 4,427,737 | 1/1984 | Cilento et al. | 428/315.7 |
| 4,530,353 | 7/1985 | Lauritzen | 206/441 |
| 4,773,409 | 9/1988 | Cilento et al. | |
| 4,930,500 | 6/1990 | Morgan | |
| 5,213,565 | 5/1993 | Rollband | 602/41 |
| 5,330,814 | 7/1994 | Fewell | 428/41 |
| 5,480,377 | 1/1996 | Cartmell et al. | 602/48 |

*Primary Examiner*—Richard J. Apley
*Assistant Examiner*—Kim M. Lee
*Attorney, Agent, or Firm*—Richard L. Miller, P.E.

[57] ABSTRACT

A self adhesive bandage roll that unrolls and covers a wounds. The roll includes a carrier strip, a gauze pad strip that is disposed on the carrier strip, and a pair of release sheets of protective material that are releasably disposed on and peelable from the carrier strip. The wound is protected by first peeling back a sufficient amount of the pair of release sheets, then affixing one end of the self adhesive bandage roll to past one extreme of the wound, then unrolling the self adhesive bandage roll longitudinally along the wound with the gauze pad strip longitudinally covering the wound and the adhesive coating adhering the self adhesive bandage roll to the area adjacent the longitudinal perimeters of the wound until the wound has been entirely covered, and then severing by severing apparatus the self adhesive bandage roll at a point past the other extreme of the wound so as to fully cover the wound and the area adjacent the longitudinal perimeters of the wound with the wound being fully covered by the gauze pad strip.

3 Claims, 1 Drawing Sheet

SELF ADHESIVE BANDAGE ROLL

BACKGROUND OF THE INVENTION

1. Field of the Invention

The present invention relates to a bandage. More particularly, the present invention relates to a self adhesive bandage roll.

2. Description of the Prior Art

Numerous innovations for bandages have been provided in the prior art that will be described. Even though these innovations may be suitable for the specific individual purposes to which they address, however, they differ from the present invention.

FOR EXAMPLE, U.S. Pat. No. 4,393,150 to Kresner teaches an adhesive bandage composition that uses a blend of polyisobutylene, polybutene, butyl rubber with reinforcing fiber, filler material and zinc oxide blended under heat and rolled into a thin sheet. The sheet of adhesive material can be attached to a bandage material on one side and covered with a protective paper on the other and cut to shape for application to a body surface.

ANOTHER EXAMPLE, U.S. Pat. No. 4,427,737 to Cilento et al. teaches a breathable tape comprising a porous backing layer and a microporous adhesive layer. The adhesive layer includes a rubbery elastomer, one or more water soluble or swellable hydrocolloids, and other optional substances and has a porosity of from about 1 to about 100 cc/sec/in2.

STILL ANOTHER EXAMPLE, U.S. Pat. No. 4,773,709 to Cilento et al. teaches an occlusive wound dressing comprising a flexible closed cell polyurethane foam, containing from about 5% to about 50% by weight of the foam of one or more water dispersible, water swellable, and/or water absorbing agents. A pressure sensitive microporous adhesive is applied or laminated to one surface of the foam as a continuous layer. A polymeric film or skin is laminated or formed on the opposite surface of the foam.

YET ANOTHER EXAMPLE, U.S. Pat. No. 4,930,500 to Morgan teaches a self adhesive bandage which comprises a hydrophilic gel located on a bandage carrier strip at the point of the strip to be positioned against a wound. Portions of the same surface of the carrier strip are also coated with a pressure sensitive adhesive, allowing the bandage to be secured to the skin. The gel-side surface is covered with a strip of removable release paper until the bandage is to be used, in order to preserve its sterility. The gel comprises water and a polyol mixed with the reaction product of a bis crosslinking agent with an acrylamide compound.

FINALLY, STILL YET ANOTHER EXAMPLE, U.S. Patent No. 5,330,814 to Fewell teaches a flexible protective cover pad that includes a backing sheet coated on one surface with a layer of adhesive and having a middle portion and a pair of side portions extending along opposite sides of the middle portion, a strip of a flexible foam material moldable to an edge of an object, and a pair of sheets of protective material releasably applied to and peelable from the adhesive-coated surface of the pair of side portions of the backing sheet. The strip of foam-like material has a greater thickness than the backing sheet and a greater width than either of the side portions of the backing sheet.

It is apparent that numerous innovations for bandages have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a self adhesive bandage roll that avoids the disadvantages of the prior art.

ANOTHER OBJECT of the present invention is to provide a self adhesive bandage roll that is simple and inexpensive to manufacture.

STILL ANOTHER OBJECT of the present invention is to provide a self adhesive bandage roll that is simple to use.

BRIEFLY STATED, YET ANOTHER OBJECT of the present invention is to provide a self adhesive bandage roll that unrolls and covers a wounds. The roll includes a carrier strip, a gauze pad strip that is disposed on the carrier strip, and a pair of release sheets of protective material that are releasably disposed on and peelable from the carrier strip. The wound is protected by first peeling back a sufficient amount of the pair of release sheets, then affixing one end of the self adhesive bandage roll to past one extreme of the wound, then unrolling the self adhesive bandage roll longitudinally along the wound with the gauze pad strip longitudinally covering the wound and the adhesive coating adhering the self adhesive bandage roll to the area adjacent the longitudinal perimeters of the wound until the wound has been entirely covered, and then severing by severing apparatus the self adhesive bandage roll at a point past the other extreme of the wound so as to fully cover the wound and the area adjacent the longitudinal perimeters of the wound with the wound being fully covered by the gauze pad strip.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows.

Figure 1:
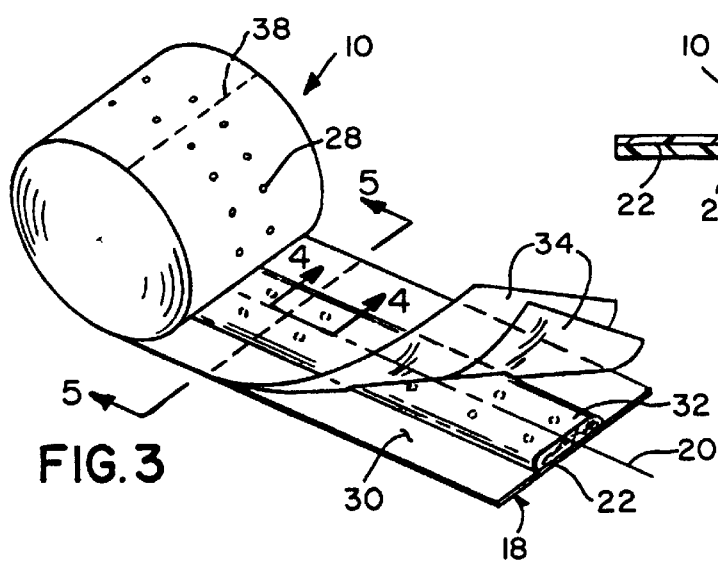
FIG. 1 is a diagrammatic perspective view of the present invention being unrolled as it extends longitudinally along and covers a wound on an arm of a person.

LIST OF REFERENCE NUMERALS UTILIZED IN THE DRAWING 10 self adhesive bandage roll of the present invention
12 wound on arm 14 of person 16
14 arm of person 16
16 person
17 area adjacent the longitudinal perimeters of wound 12
18 carrier strip
20 longitudinal axis of carrier strip 18
22 wound facing surface of carrier strip 18
24 middle portion of carrier strip 18

26 pair of side portions of carrier strip 18
28 plurality of breathing throughbores in middle portion 24 of carrier strip 18
30 adhesive coating on wound facing surface 22 of carrier strip 18
32 gauze pad strip
34 pair of release sheets
36 scissors
38 plurality of spaced-apart perforation lines in self adhesive bandage roll 10

DETAILED DESCRIPTION OF THE PREFRRED EMBODIMENT

Figure 2:
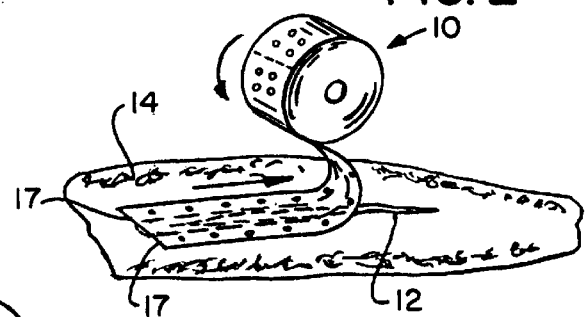
FIG. 2 is an enlarged diagrammatic perspective view of the area generally enclosed by the dotted ellipse identified by arrow 2 in FIG. 1.
Figure 5:
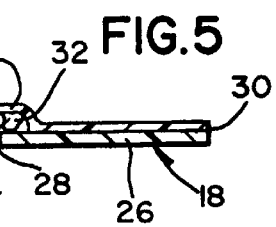
FIG. 5 is an enlarged cross sectional view, with parts broken away, taken on line 5—5 in FIG. 3.

Referring now to the figures in which like numerals indicate like parts, and particularly to FIGS. 1 and 2, the self adhesive bandage roll of the present invention is shown generally at 10 being unrolled as it extends longitudinally along and covers a wound 12 on an arm 14 of a person 16, with the wound 12 having an area adjacent the longitudinal perimeters 17 of the wound 12.

Figure 3:
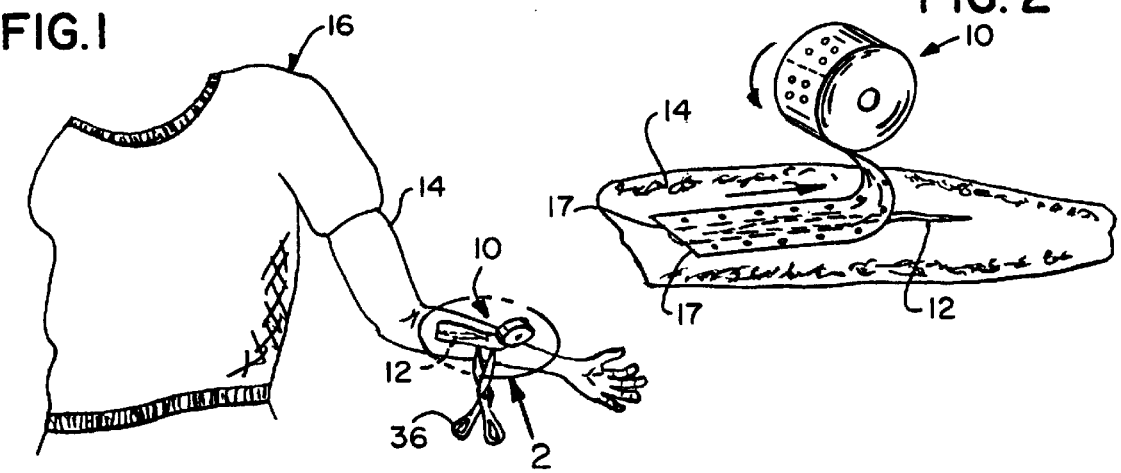
FIG. 3 is an diagrammatic perspective view of the present invention.
Figure 4:
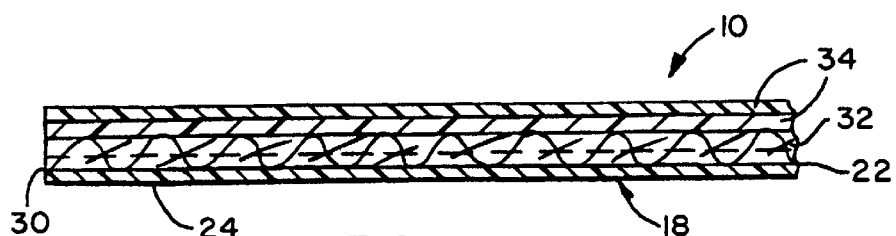
FIG. 4 is an enlarged cross sectional view, with parts broken away, taken on line 4—4 in FIG. 3.

The configuration of the self adhesive bandage roll 10 of the present invention can best be seen in FIGS. 1, 2 and 3, and as such will be discussed with reference thereto.

The self adhesive bandage roll 10 includes a carrier strip 18 that is slender, elongated, and formed in a roll, and has a length, a longitudinal axis 20, and a wound facing surface 22 that faces the wound 12 when the self adhesive bandage roll 10 is being utilized.

The carrier strip 18 comprises three longitudinal portions that are slender and elongated and include a middle portion 24 that extends along the longitudinal axis 20 of the carrier sheet 18 and a pair of side portions 26 that extend longitudinally along opposite sides of the middle portion 24 of the carrier strip 18.

The middle portion 24 of the carrier strip 18 has a plurality of breathing throughbores 28 that extend therethrough and which are spaced longitudinally therealong.

The self adhesive bandage roll 10 further includes an adhesive coating 30 that covers the wound facing surface 22 of the carrier strip 18, in its entirety, and adheres an appropriate amount of the self adhesive bandage roll 10 to the area adjacent the longitudinal perimeters 17 of the wound 12 when the self adhesive bandage roll 10 is being utilized.

The self adhesive bandage roll 10 further includes a gauze pad strip 32 that is slender, elongated, and affixed to and disposed on the middle portion 24 of the wound facing surface 22 of the carrier strip 18, by the adhesive coating 30, and extends longitudinally along the entire length of and has a width less than the carrier strip 18.

The gauze pad strip 32 contacts the wound 12 longitudinally when the self adhesive bandage roll 10 is being utilized, and is in communication with the plurality of breathing throughbores 28 in the middle portion 24 of the carrier strip 18 so as to allow the wound 12 to breath when the self adhesive bandage roll 10 is being utilized.

The self adhesive bandage roll 10 further includes a pair of release sheets 34 of protective material that are slender, elongated, and releasably disposed on and peelable from the adhesive coating 30 available on the pair of side portions 26 of the carrier strip 18, and overlap each other on the gauze pad strip 32 so as to facilitate removal thereof while protecting the gauze pad strip 32.

The method of utilizing the self adhesive bandage roll 10 will now be discussed.

STEP 1: Peel back a sufficient amount of the pair of release sheets 34.

STEP 2: Affix one end of the self adhesive bandage roll 10 to past one extreme of the wound 12.

STEP 3: Unroll the self adhesive bandage roll 10 longitudinally along the wound 12, with the gauze pad strip 32 longitudinally covering the wound 12 and the adhesive coating 30 available on the pair of side portions 26 of the carrier strip 18 adhering the self adhesive bandage roll 10 to the area adjacent the longitudinal perimeters 17 of the wound 12, until the wound 12 has been entirely covered.

STEP 4: Sever the self adhesive bandage roll 10 at a point past the other extreme of the wound 12 so as to fully cover the wound 12 and the area adjacent the longitudinal perimeters 17 of the wound 12, with the wound 12 being fully covered by the gauze pad strip 32. Severing can be accomplished by the use of scissors 36 as shown in FIG. 1 or as shown in FIG. 3 the self adhesive bandage roll 10 can be provided with a plurality of spaced-apart perforation lines 38 that extend laterally thereacross at predetermined intervals.

It will be understood that each of the elements described above, or two or more together, may also find a useful application in other types of constructions differing from the types described above.

While the invention has been illustrated and described as embodied in a self adhesive bandage roll, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A self adhesive bandage roll that unrolls and covers a wound that has an area adjacent its longitudinal perimeters, comprising:
    a) a carrier strip;
    b) a gauze pad strip disposed on said carrier strip; and
    c) a pair of release sheets of protective material releasably disposed on and peelable from said carrier strip, wherein said carrier strip is slender, elongated, and formed in a roll, and has a length, a longitudinal axis, and a wound facing surface that faces the wound when said self adhesive bandage roll is being utilized, wherein said carrier strip comprises three longitudinal portions that are slender and elongated and include a middle portion that extends along said longitudinal axis of said carrier sheet and a pair of side portions that extend longitudinally along opposite sides of said middle portion of said carrier strip, wherein said middle portion of said carrier strip has a plurality of breathing throughbores that extend therethrough and which are spaced longitudinally therealong, further comprising an adhesive coating covering said wound facing surface of said carrier strip, in its entirety, and adhering an appropriate amount of said self adhesive bandage roll to the area adjacent said longitudinal perimeters of the wound when said self adhesive bandage roll is being utilized, wherein said gauze pad strip is slender, elongated, and affixed to and disposed on said middle portion of said wound facing surface of said carrier strip, by said adhesive coating, and extends longitudinally along said entire length of said carrier strip and has a width less than said carrier strip; said gauze pad strip contacts and covers the wound longitudinally when said self adhesive bandage roll is being utilized, and is in communication with said plurality of breathing throughbores in said middle portion of said carrier strip so as to allow the wound to breath when said self adhesive bandage roll is being utilized.

2. The self-adhesive bandage roll as defined in claim 1, wherein said pair of release sheets of protective material are slender, elongated, and releasably disposed on and peelable from said adhesive coating available on said pair of side portions of said carrier strip, and overlap each other on said gauze pad strip so as to facilitate removal thereof while protecting said gauze pad strip, with the wound being protected by first peeling back a sufficient amount of said pair of release sheets, then affixing one end of said self adhesive bandage roll to past one extreme of the wound, then unrolling said self adhesive bandage roll longitudinally along the wound with said gauze pad strip longitudinally covering the wound and said adhesive coating available on said pair of side portions of said carrier strip adhering said self adhesive bandage roll to the area adjacent the longitudinal perimeters of the wound until the wound has been entirely covered, and then severing by severing means said self adhesive bandage roll at a point past the other extreme of the wound so as to fully cover the wound and the area adjacent the longitudinal perimeters of the wound with the wound being fully covered by said gauze pad strip.

3. The self-adhesive bandage roll as defined in claim 2, wherein said severing means is one of scissors and a plurality of spaced-apart perforation lines that extend laterally across said self adhesive bandage roll at predetermined intervals.

\* \* \* \* \*